United States Patent [19]

Georgalas et al.

[11] Patent Number: 4,837,019
[45] Date of Patent: Jun. 6, 1989

[54] SKIN TREATMENT COMPOSITION AND METHOD FOR TREATING BURNED SKIN

[75] Inventors: Arthur C. W. Georgalas, Leonardo; George E. Deckner, Westfield, both of N.J.

[73] Assignee: Charles of the Ritz Group Ltd., New York, N.Y.

[21] Appl. No.: 895,403

[22] Filed: Aug. 11, 1986

[51] Int. Cl.[4] .......................... A61K 37/02; A61K 7/48
[52] U.S. Cl. ........................ 424/101; 424/59; 424/60; 424/81; 424/DIG. 13; 514/2; 514/802
[58] Field of Search ................... 424/101, 59, 60, 81, 424/DIG. 13; 514/802, 2

[56] References Cited

U.S. PATENT DOCUMENTS 4,455,300 6/1984 Wallace et al. .................. 424/101
4,478,853 10/1984 Chaussee ............................. 424/59

OTHER PUBLICATIONS

Mausner, cited in Chem. Abstracts vol. 95: 12580p, 1981.
Key Pharmaceuticals, cited in Chem. Abstracts vol. 93: 210253f, 1980.
Kobayashi Kose Co., Ltd., cited in Chem. Abstracts vol. 101: 116577b, 1984.
Strianse, in Cosmetics: Science and Technology, vol. 1, 1972, pp. 196–197.

*Primary Examiner*—Ronald W. Griffin
*Assistant Examiner*—Jacqueline M. Stone
*Attorney, Agent, or Firm*—Lerner, David, Littenberg, Krumholz & Mentlik

[57] ABSTRACT

Skin treatment compositions are provided which counteract moisture loss and promote healing of burned or sunburned skin which include a unique moisturizing component formed of polyglycerylmethacrylate, glycerine, allantoin, panthenol, amino acid complex, and fibronectin.

15 Claims, No Drawings

SKIN TREATMENT COMPOSITION AND METHOD FOR TREATING BURNED SKIN

FIELD OF THE INVENTION

The present invention relates to an improved skin treatment composition which counteracts moisture loss and promotes healing of burned skin or sunburned skin and to a method for treating such burned skin by applying such skin treatment composition to the skin.

BACKGROUND OF THE INVENTION

Aging and burning of skin are similar in that they each rob the skin of moisture and thus deplete oxygen and nourishment. Accordingly, bring moisture to either aging skin or burned skin and you bring oxygen and nourishment which are vital to the skin repairing itself.

Until now, skin moisturizer compositions have been available which contain animal, vegetable and/or mineral oils which impart a greasy feel to the compositions and thus may stain clothes. To overcome this problem, it has been suggested to employ aqueous-based moisturizers. Although various aqueous-based moisturizers have achieved some degree of commercial success, they have been far from satisfactory in actually replenishing moisture in aging and/or burned skin.

DESCRIPTION OF THE INVENTION

This invention is directed to improved non-greasy skin treatment compositions for replenishing moisture in the skin, especially burned skin or sunburned skin, and which includes a moisturing component formed of a combination of various moisturizing and wound healing compounds, debriding agents and cell growth stimulants, which moisturizing component is present in an amount within the range of from about 2 to about 30% by weight and preferably from about 5 to about 15% by weight of the composition.

In addition, depending upon the form that the skin treatment composition of the invention will take, it will also include water, at least one emulsifier and/or thickener and/or bodying agent, and at least one preservative, and optionally may contain one or more chelating agents, one or more gelling agents, one or more emollients, one or more other humectants, one or more sun screen agents, and/or one more fragrances and/or one or more coloring agents.

The skin treatment composition of the invention is preferably an oil-in-water type emulsion since this type of emulsion affords better cosmetic feel to the product. However, the product could also be formulated as a water-in-oil emulsion, cream base, gel, aqueous/alcoholic or glycol solution or microemulsion. Depending upon the choice of ingredients, the formulation has a semi-solid cream-like consistency which can be packaged in a plastic squeeze tube, a lotion type consistency which can be packaged in a plastic squeeze container, an ointment-type consistency which can be packaged in a squeeze type container or a liquid consistency which may be packaged in a bottle. The container can include a flow-type cap or pump-type dispenser.

In addition, in accordance with the present invention, a method is provided for treating burned or sunburned skin to promote healing which includes the step of applying to the skin an effective amount of a skin treatment composition as disclosed herein.

The skin treatment composition of the invention may take the form of a location, cream, liquid, or ointment.

The moisturizing component of the composition of the invention will include polyglyceryl methacrylate which serves as a film-former and moisturizer in an amount within the range of from about 1 to about 10% and preferably from about 3 to about 7% by weight of the moisturizing component, glycerine which serves as a humectant-moisturizer in an amount within the range of from about 1 to about 8% and preferably from about 2 to about 5% by weight of the moisturizing component; allantoin (which may be in the form of a complex of allantoin and N-acetyl dl methionine) which has cellular stimulating activity, increases cellular respiration, increases water binding properties of the stratum corneum and promotes normal cell sloughing, in an amount within the range of from about 0.1 to about 0.5% and preferably from about 0.1 to about 0.4% by weight of the moisturizing component, panthenol (d- or dl-) which serves to accelerate healing of various types of burns, has moisturizing properties and easily penetrates the epidermis and has smoothing anti-inflammatory properties on skin, in an amount within the range of from about 0.5 to about 5% and preferably from about 1 to about 3% by weight of the moisturizing component; amino acid complex which includes proline, arginine, pyrrolidone carboxylic acid and optionally glycine, which serves to penetrate skin to promote moisture retention with the epidermis and stimulate cell growth, in an amount within the range of from about 0.05 to about 5% and preferably from about 0.1 to about 2% by weight of the moisturizing component, and fibronectin aqueous solution which serves to enhance cell to cell adhesion and thus promotes wound healing in an amount within the range of from about 0.005 to about 1.5% and preferably from about 0.007 to about 0.3% by weight of the moisturizing component (said fibronectin being formulated as an 0.2 to 5% aqueous solution).

The polyglycerylmethacrylate component is in the form of a white transparent gel containing from about 50 to about 75% by weight solids, and may or may not contain incidental ingredients, such as propylene glycol which may be present in an amount of 2% or less (preferably about 1%). A preferred polyglycerylmethacrylate is Lubrajel, a registered trademark of United Guardian Inc., which is distributed by Meadow Technical Corp., Livingston, N.J. A preferred form of Lubrajel as a 9% solution has a viscosity at 25° C. (Brookfield RVT, spindle No. 4, at 50 rpm) ranging from about 700 to about 1,000 cps, a specific gravity of 1 to 1.2 mg/ml, is completely soluble in water and is substantially stable at 25020 F. Lubrajel is a clathrate formed by the reaction of glycerin and methylmethacrylate.

The polyglycerylmethacrylate may be employed by itself or as a dispersion with other polyols, such as propylene glycol or any of the polyols mentioned hereinafter, in amounts of 2% or less, preferably about 1%.

In general, regardless of the form of the skin treatment composition of the invention, it will include from about 2 to about 30%, and preferably from about 5 to about 15% by weight of the moisturizing component, from about 50 to about 90% and preferably from about 60 to about 80% by weight water, from about 0 to about 25% and preferably from about 2 to about 10% by weight of one or more other humectants, from about 1 to about 10% and preferably from about 1 to about 5% by weight of one or more emulsifiers when the composition is a cream, lotion, or gels, from about 0.05 to about 10% and preferably from about 0.05 to about 8% by weight of one or more thickeners, wax bodying agent or gelling agents where the composition is a cream or lotion or gel, from about 0.05 to about 2% and preferably from about 0.1 to about 1% by weight of one or more preservatives, and the following optional ingredients: from about 0.01 to about 0.5% and preferably from about 0.05 to about 0.1% by weight of one or more chelating agents, from about 1 to about 30% and preferably from about 1 to about 10% by weight of one or more emollients when the composition is a cream, lotion or gel, from about 1 to about 50% and preferably from about 5 to about 10% by weight of one or more solvents, from about 1 to about 15% and preferably from about 1.5 to about 10% by weight of one or more sun screen agents, less than about 1% by weight of one or more fragrances and/or less than about 1% by weight of one or more colorants. In addition, the skin treatment composition of the invention may also optionally include various other conventional ingredients normally employed in skin conditioning or moisturizing compositions or sunscreen compositions such as skin conditioning agents, moisturizers, waxes, polymers or other active ingredients.

Suitable preservatives include imidazoli-dinyl urea (Germall 115), diazolidinyl urea (Germall II), methylparaben (Tegosept M), quaternium-15 (N-(3-chloroallyl)hexaminium chloride, Dowicil 200), propylparaben (Tegosept P), dimethyldimethoyl hydantoin, benzyl alcohol and/or phenoxyethanol, etc., and a preferred antioxidant is a mixture of butylated hydroxyanisole, propylene glycol, propyl gallate and citric acid (Tenox 2). The formation will preferably contain the antioxidant mixture and one or more of the preservatives or any other preservatives and antioxidants approved for cosmetic use.

Where the skin treatment composition of the invention is in the form of a lotion, cream, or ointment, it will preferably include one or more emulsifiers, thickeners, humectants and emoillients.

Suitable emulsifiers include polyethylene glycol 20 sorbitan monolaurate (Polysorbate 20), polyethylene glycol 5 soya sterol, sorbitan tristearate, sorbitan trioleate, glyceryl, monopalmitate, diethanolamine cetyl phosphate, glyceryl monopalmitate, glyceryl monostearate, polyethylene glycol 100 stearate, polyethylene glycol 20 stearyl ether (Brij 78, Steareth 20), polyethylene glycol ether of lauryl alcohol (Laureth 23), polysorbate 80 (Tween 80), lecithin, etc. The formulation will preferably contain a mixture of two or more of these emulsifiers or others which are approved for cosmetic use.

Thickeners, gelling agents or wax-bodying agents which may be present include Carbopol 934 or Carbomer 940 which is a hydrophilic acrylic polymer cross-linked with a polyfunctional agent and employed with an organic or inorganic base, preferably triethanolamine. Other examples of thickeners which may be employed herein include, but are not limited to, stearic acid, fatty alcohols, such as cetyl alcohol, stearyl alcohol, magnesium aluminum silicate, dimethicone, stearoxydimethicone, hydroxyethyl cellulose, propylene glycol monostearate, glyceryl monostearate, hydroxypropyl cellulose, carboxy-methyl cellulose, xanthan gum, myristyl stearate, or cetyl stearate.

Suitable emollients include glyceryl monooleate, myristyl alcohol, isopropyl palmitate, $C_{12}$-$C_{15}$-alcohol benzoates (Finsolv TN), octyl palmitate, propylene glycol dicaprylate/dicaprate, isopropyl myristate, diisopropyl dimerate (that is, the diester of isopropyl alcohol and dimer acid), dimethicone, stearoxydimethicone, and the like. The formulation will preferably contain a mixture of several of these emollients or others which are approved for cosmetic use.

Skin conditioning agents which may optionally be present in the composition of the invention include hydrolyzed animal protein as disclosed in U.S. Pat. No. 4,374,766. Such conditioning agents may be present in an amount within the range of from about 0.01 to about 10% and preferably from about 0.05 to about 2% by weight and optimally from about 0.1 to about 2% by weight depending upon the ultimate use of the skin preparation.

Humectants which may be present include propylene glycol, glycerine or polyethylene glycol wax (such as Carbowax 400).

Chelating agents for sequestering metal ions in aqueous solution which may be present herein include disodium ethylenediamine tetraacetic acid, EDTA, tetrasodium EDTA, or citric acid.

As indicated, the skin treatment compositions of the invention may include one or more known ultraviolet absorbing agents, preferably at least one compound which absorbs in the UV-B region (wavelength 290 to 320 nanometers) and optionally one or more other compounds which absorb in the UV-A region (wavelength 320 to 400 nanometers). The total amount of UV absorbing agents included within the formulation will be from about 2% to about 15% by weight, which amount will determine whether it is a sunscreen or sunblock.

Suitable UV-A absorbing agents which may be employed include 2-(2'-hydroxy-5'-methylphenyl)-benzotriazole (Tinuvin P); 2-(2'-hydroxy-5'-t-octyl-phenyl)-benzotriazole (Spectra-Sorb UV 5411); 2,4-dihydroxybenzophenone (Uvinul 400); 2-hydroxy-4-methoxybenzophenone (oxybenzone, Spectra-Sorb UV9, Uvinul M-40); 2,2',4,4'-tetrahydroxybenzophenone (Uvinul D50); 2,2'-dihydroxy-4,4'-dimethoxybenzophenone (Uvinul D49); 2,2'-dihydroxy-4-methoxy-benzophenone (dioxybenzone, Spectra-Sorb UV24); 2-ethylhexyl-4-phenyl-benzophenone carbonate (Eusolex 3573); 2-hydroxy-4-methoxy-4'-methyl-benzophenone (mexenone, Uvistat 2211); 2-hydroxy-4-(n-octyloxy)benzophenone (octabenzone, Spectra-Sorb UV531); 4-phenylbenzophenone (Eusolex 3490); and 2-ethylhexyl-2-cyano-3,3'-diphenylacrylate (Uvinul N539); butyl methoxydibenzoyl methane (Parsol 1789), and benzphthalide (Escalol 547) as well as water-soluble sunscreens such as sulisobenzone. The UV-A absorbing agent or agents are present in the final product at from 0 to about 10% by weight of the formulation. The amount will vary according to the particular agent selected and whether the formulation is intended to minimize or permit tanning. Where a UV-A absorbing agent is employed, the preferred UV-A absorbing agent is 2-hydroxy-4-methoxybenzophenone alone or in combination with 2,2'-dihydroxy-4-methoxy-benzo-phenone.

Suitable UV-B absorbing agents include 4-(dimethylamino)benzoic acid, ethyl ester; 4-(dimethylamino)benzoic acid, 2-ethylhexyl ester (Escalol 507); 4-(dimethylamino)benzoic acid, pentyl ester (Escalol 506); glyceryl p-amino-benzoate (Excalol 106); isobutyl p-amino-benzoate (Cycloform); and isopropyl p-amino-benzoate; 2-ethylhexyl methoxy cinnamate (Parsol MCX); phenylbenzimidazole sulfonic acid (Eusolex 232) which is water-soluble when converted to its known salts; homomenthyl salicylate, and ethyl hexyl salicylate and diethanolamine methoxy cinnamate (Parsol Hydro, water-soluble). The UV-B absorbing agent or agents are present in the final product at from about 1% to about 15% by weight of the formulation. The amount will vary according to the particular agent selected and degree of protection desired in the final product. The preferred UV-B absorbing agent is 4-(dimethylamino)benzoic acid, 2-ethyl-hexyl ester (Escalol 507).

Where the skin treatment composition is in the form of a location, cream, or liquid, any other active ingredients that may be present will be "all-in-solution" (i.e., solubilized or emulsified) so that substantially no active ingredient crystallizes out at room temperature.

With regard to the cream formulations of the invention where the active ingredients are to be all-in-solution, the cream will contain from about 2 to about 30% and preferably from about 5 to about 15% by weight of the moisturizing component based on the weight of the entire cream formulation; from about 0.05 to about 10% and preferably from about 3 to about 7% by weight based on the weight of the entire cream formulation of a thickneer or wax bodying agent, such as Carbomer 940, cetyl alcohol and/or stearic acid and/or other thickeners or bodying agents as set out above. The all-in-solution cream formulation will also include in the oil phase, from about 2 to about 15% and preferably from about 5 to about 10% by weight of the emulsifier-thickener based on the weight of the entire cream formulation, and from about 2 to 30% and preferably from about 3 to about 15% by weight of emollient based on the weight of the entire cream formulation. The oil phase may also include one or more preservatives similar to that present in the aqueous phase described below.

The aqueous phase of the all-in-solution cream formulation may contain a glycol type preservative or humectant such as propylene glycol and/or a paraben or other conventional type perservative such methyl and/or propyl paraben, and purified water in amount within the range of from about 30 to about 80% by weight and preferably from about 35 to about 65% by weight of the entire cream formulation.

With regard to the lotion formulation of the invention where the moisturizing component is to be all-in-solution, the lotion will contain from about 0.01 to about 5% and preferably from about 0.1 to about 0.5% by weight of the moisturizing component based on the weight of the entire lotion formulation. The active ingredient in the all-in-solution lotion formulation can have part of it also solubilized in the oil phase. The lotion may contain from about 1 to 10% and preferably from about 2 to about 5% by weight emulsifier-thickener based on the weight of the entire lotion formulation, and from about 2 to about 20% and preferably from about 4 to about 10% by weight of emollient based on the weight of the entire lotion formulation. The oil phase may also optionally include one or more preservatives.

The aqueous phase of the all-in-solution lotion formulation may contain one or more preservatives and purified water in an amount within the range of from about 60 to about 90% by weight and preferably from about 70 to about 85% by weight of the entire lotion formulation.

Where the moisturizing component is to be employed in liquid solution, the concentration of moisturizing component will be in amounts ranging from about 2 to about 30% by weight together with from about 5 to about 15% by weight aqueous solvent therefor.

The gel formulation of the invention is preferably in the form of a hydrophilic clear gel, and will contain from about 2 to about 30%, and preferably from about 5 to about 15% by weight of the moisturizing component based on the weight of the entire formulation, and from about 30 to about 95% and preferably from about 50 to about 80% by weight of water based on the weight of the entire formulation. The gel formulation may also include one or more humectants, preservatives, antioxidants, water-soluble sunscreens and one or more gelling agents or bodying agents (in an amount within the range of from about 0.2 to about 20% by weight and preferably from about 0.5 to about 10%) such as Carbomer 940 or 934, Lubragel, hydroxymethylpropyl cellulose, propylene glycol alginate or other algal gums, such as Seamollient.

In formulating the aqueous gel, unless otherwise indicated, the viscous ingredients may be employed in amounts indicate hereinbefore.

Examples of preferred formulations in accordance with the present invention include, but are not limited to, the following:

|  | Range in % by weight of moisturizing component |
| --- | --- |
| Moisturizing component | |
| Polyglycerylmethacrylate | 3 to 7 |
| Glycerine | 2 to 5 |
| Allantoin | 0.1 to 0.4 |
| Panthenol | 1 to 3 |
| Amino acid complex | 0.1 to 2 |
| Fibronectin (as an 0.4% aqueous solution | 0.007 to 0.3* |

|  | Range in % by weight of total formulation |
| --- | --- |
| Cream formulation | |
| Moisturizing component | 5 to 15 |
| Solvents | 5 to 10 |
| Emulsifiers | 2 to 5 |
| Thickeners | 2 to 20 |
| Humectant | 2 to 20 |
| Chelating Agent | 0.05 to 0.1 |
| Water | 50 to 80 |
| Preservatives | 0.2 to 1 |
| Lotion formulation | |
| Moisturizing component | 5 to 15 |
| Solvents | 5 to 10 |
| Emulsifiers | 1 to 5 |
| Thickeners | 1 to 10 |
| Humectants | 2 to 10 |
| Chelating Agents | 0.05 to 0.1 |
| Water | 60 to 90 |
| Preservatives | 0.2 to 1 |
| Solution or Liquid formulation | |
| Moisturizing component | 5 to 15 |
| Water | 75 to 90 |
| Humectants, preservatives, sunscreens, chelating agents, antioxidants | 5 to 10 |
| Aqueous gel | |
| Moisturizing component | 5 to 15 |
| Water | 50 to 80 |
| Gelling agent | 0.5 to 10 |
| Humectants, preservatives, sunscreens chelating agents, antioxidants | 5 to 10 |

(*Fibronectin by itself - 0.000028 to 0.0012%)

The various formulations of the invention may be presented employing conventional procedures as outlined in the working examples.

EXAMPLE 1

A skin treatment composition in the form of a cream of the following composition was prepared as described below.

| Cream Formulation | |
|---|---|
| Ingredient | Parts by Weight |
| Blend I | |
| Deionized water | 73 |
| Carbopol 940 (bodying agent) | 0.5 |
| Allantoin (part of moisturizing component) | 0.2 |
| DL-Panthenol (part of moisturizing component) | 1.5 |
| Simethicone (anti-foam agent) | 0.1 |
| Blend II | |
| Polyglycerylmethacrylate (Lubragel) } part of moisturizing component | 5 |
| Glycerine | 3 |
| Blend III | |
| Propylene glycol (humectant) | 1 |
| Methyl paraben (preservative) | 0.2 |
| Blend IV | |
| Laureth 23 (Brij 35) (emulsifier) | 2 |
| $C_{12}$-$C_{15}$ alcohol benzoates (Finsolv TN) (emulsifier) | 4 |
| Propylene glycol dicaprylate/dicaprate (Miglyol 840, emulsifier) | 2 |
| Propyl paraben (preservative) | 0.1 |
| Cetyl alcohol } thickener | 1.5 |
| Stearic acid | 1.5 |
| Sorbitan monostearate (emulsifier) | 1 |
| Blend V | |
| Deionized water | 1.3 |
| Triethanolamine (thickener) | 1 |
| Blend VI | |
| Dimethyldimethoyl hydantoin (Glydant) | 0.3 |
| Blend VII | |
| Deionized water | 1 |
| Fibronectin | 0.01 |
| L-Proline } part of moisturizing component | 0.05 |
| L-Arginine | 0.1 |
| Pyrrolidone carboxylic acid (Ajidew A-100) | 0.05 |

Blend I was prepared by charging deionized water to a sweep kettle equipped with a homomixer; the Carbopol 940 was added and the mixture was homomixed for 30 minutes; the allantoin was added and the mixture was homomixed for 2 minutes; DL-Pantenol was added and the mixture was homomixed for 2 minutes; and the simethicone was added and the mixture was homomixed for 1 minute. When the mixture was uniform, it was sweep-mixed while heating at 78 to 80° C.

Blend IV was prepared by mixing all of the Blend IV ingredients except the sorbitan monostearate, propeller mixing while heating to 78 to 80° C., at 78 to 80° C. adding sorbitan monostearate and propeller mixing at 78 to 80° C.

The Blend III ingredients were mixed with propeller mixing while heating at 40 to 45° C.

The Blend II ingredients were added to Blend I with sweep mixing and heating at 78 to 80° C.

The Blend V ingredients were premixed.

When the Blend I-II mixture was at 78-80° C. the Blend III mix was added to Blend I-II and the mixture was sweep mixed at 78-80° C. to form Blend I, II, and III mix.

The Blend IV mix (heated at 78 to 80° C.) was added to the Blend I-II-III mix (heated at 78 to 80° C.), and the Blend I to IV mixture was fast sweep mixed for 30 minutes at 78 to 80° C. and then slow sweep mixed for 30 minutes.

Blend V was added to the Blend I to IV mixture and the mix was speed mixed for 30 minutes and then slow sweep mixed for 20 minutes while at 51° C. The Blend I to IV was cooled to 40° C. nd Blend VI was added thereto to form Blend I to VI.

The Blend VII ingredients were premixed and Blend VII was added to Blend I to VI and the mixture was sweep mixed for 10 minutes and cooled to 30° C. ot form the cream of the invention.

EXAMPLE 2

A skin treatment formulation in the form of a lotion of the following composition was prepared as described below.

| Lotion Formulation | |
|---|---|
| Ingredient | Parts by Weight |
| Blend I | |
| Deionized water | 71 |
| Sequestered $Na_2$ EDTA (chelating agent) | 0.1 |
| Carbopol 940 (bodying agent) | 0.15 |
| Allantoin (part of moisturizing component) | 0.2 |
| dl-Panthenol (part of moisturizing component) | 1.5 |
| Blend II | |
| Polyglycerylmethacrylate-) (Lubrajel) } part of moisturizing component | 5 |
| Glycerine | 3 |
| Blend III | |
| Propylene glycol | 1 |
| Xanthan gum | 0.1 |
| Blend IV | |
| Stearic acid (thickener) | 1.4 |
| $C_{12}$-$C_{15}$ Alcohol benzoates (emollient) | 4 |
| Propylene glycol dicaprylate/dicaprate | 2 |
| Diisopropyl dimerate (Schercemol DID, emollient) | 2 |
| Cetyl alcohol (bodying agent) | 0.8 |
| Steareth 20 (Brij 78, emulsifier) | 1.3 |
| Polysorbate 60 (Tween 60, emulsifier) | 1.3 |
| Blend V | |
| Deionized water | 0.23 |
| Triethanolamine (thickener) | 0.23 |
| Blend VI | |
| Deionized water | 1 |
| Imidizolidinyl urea (preservative) | 0.4 |
| Quaternium 15 (chloroallyl methenamine chloride) (preservative) | 0.2 |
| Blend VII | |
| Deionized water | 1 |
| L-Proline | 0.01 |
| L-Arginine } Part of moisturizing component | 0.02 |
| Pyrrolidone carboxylic acid | 0.01 |
| Glycine | 0.2 |
| Fibronectin | 0.01 |
| Fragrance | 0.02 |

The Example 2 lotion was prepared in a manner similar to that described in Example 1 except that heating was carried out at 75 to 78° C. as opposed to 78 to 80°

C. and propeller mixing was preferred over sweep mixing.

EXAMPLE 3

Aqueous Gel

| Ingredient | Parts by Weight |
| --- | --- |
| Moisturizing component as described in Example 1 | 10 |
| Carbomer 940 (gelling agent) | 0.5 |
| Water | 88.5 |
| Triethanol amine (neutralizing agent) | 0.5 |
| Germall II (preservative) | 0.2 |
| Glydant (preservative) | 0.3 |

Carbomer 940 is dispersed in 87 parts water with propeller mixing. The ingredients in the moisturizing component are mixed together with propeller mixing and the mix is added to the Carbomer 940 solution. Triethanolamine is then added to the mixture with sweep mixing until a gel forms. The Glydant and Germall II are dissolved in 1.5 parts water and this solution is added to the gel with mixing to form the aqueous gel of the invention.

What is claimed is:

1. A skin treatment composition which counteracts moisture loss and promotes healing of burned or sunburned skin, in the form of an ointment, cream, lotion or liquid, comprising water, at least one preservative and between about 2% and about 30% by weight of a moisturizing component which is comprised of polyglyceryl methacrylate, glycerine, allantoin, panthenol, fibronectin and an amino acid complex including proline, arginine, and pyrrolidone carboxylic acid.

2. The composition as defined in claim 1 wherein the moisturizing component is present in an amount within the range of from about 5 to about 15% by weight of the composition.

3. The composition as defined in claim 1 wherein said composition is the form of a lotion, cream, solution or aqueous gel.

4. The composition as defined in claim 1 wherein the moisturizing component is comprised of from about 1 to about 10% by weight polyglyceryl-methacrylate, from about 1 to about 8% by weight glycerine, from about 0.1 to about 0.5% by weight allantoin, from about 0.5 to about 5% by weight panthenol, from about 0.05 to about 5% by weight amino acid complex and from about 0.005 to about 1.5% by weight fibronectin (based on a 0.2 to 5% aqueous solution) all of the above % being based on the weight of the moisturizing component.

5. The composition as defined in claim 1, wherein the amino acid complex includes glycine.

6. The composition as defined in claim 1 further including a chelating agent which is disodium ethylene diamine tetracetic acid, citrate, tetrasodium EDTA or citric acid.

7. The composition as defined in claim 1 in the form of a cream, lotion or gel and further including a thickener-gelling agent which is a cross-linked acrylic acid polymer and triethanolamine as a neutralizer for such polymer, xanthan gum, magnesium aluminum silicate, hydroxyethyl cellulose or carboxymethyl cellulose.

8. The composition as defined in claim 3 which further includes a humectant selected from the group consisting of propylene glycol, polyethylene glycol, glycerine, sorbitol and butylene glycol.

9. The composition as defined in claim 1 which further includes an emulsifier-thickener selected from the group consisting of polytheylene glycol 5, soya sterol, polyethylene glycol ether, lauryl alcohol, and glyceryl monostearate.

10. The composition as defined in claim 1 further including an emollient.

11. The composition as defined in claim 10 wherein the emollient is dimethicone, stearoxy-dimethicone or diisopropyl dimerate.

12. The composition as defined in claim 1 wherein the preservative is benzyl alcohol, phenoxyethanol, butyl paraben, propylparaben, diazolidinyl urea, methyl paraben, imidazolidinyl 13. A method for promoting healing of and counteracting moisture loss from burned skin, which comprises applying to the skin of a mammalian, in need of such treatment, an effective amount of a skin treatment composition as defined in claim 1.

14. The composition of claim 1, which further includes an additive selected from the group consisting of humectants, emulsifiers, thickeners and mixtures thereof.

15. A method for promoting healing of and counteracting moisture loss from sunburned skin, which comprises applying to the skin of a mammalian an effective amount of a skin treatment composition as defined in claim 1.

* * * * *

UNITED STATES PATENT AND TRADEMARK OFFICE
CERTIFICATE OF CORRECTION

PATENT NO. : 4,837,019

DATED : June 6, 1989

INVENTOR(S) : Georgalas et al.

It is certified that error appears in the above-identified patent and that said Letters Patent is hereby corrected as shown below:

Column 2, line 2, "location" should read --lotion--.
Column 2, line 22, "smoothing" should read --soothing--.
Column 2, line 52, "25020" should read --250°--.
Column 3, line 33, "formation" should read --formulation--.
Column 5, line 12, "location" should read --lotion--.
Column 7, line 2, "presented" should read --prepared--.
Column 8, line 9, "speed" should read --sweep--.
Column 10, line 33, after "paraben, imidazolidinyl" insert --urea, dimethyldimethoyl hydantoin, or mixtures of two or more thereof.--.

Signed and Sealed this

Twentieth Day of March, 1990

Attest:

JEFFREY M. SAMUELS

Attesting Officer

Acting Commissioner of Patents and Trademarks